United States Patent [19]

Ririe

[11] 4,067,226
[45] Jan. 10, 1978

[54] CHROMATOGRAPHIC APPARATUS

[75] Inventor: Otis E. Ririe, Bartlesville, Okla.

[73] Assignee: Phillips Petroleum Company, Bartlesville, Okla.

[21] Appl. No.: 711,030

[22] Filed: Aug. 2, 1976

[51] Int. Cl.² .................................................. G01N 31/08
[52] U.S. Cl. ............................................................ 73/23.1
[58] Field of Search ........... 73/23.1; 23/232 C, 254 R

[56] References Cited

U.S. PATENT DOCUMENTS

| | | | |
|---|---|---|---|
| 3,103,807 | 9/1963 | Broerman | 73/23.1 |
| 3,236,092 | 2/1966 | Carter | 73/23.1 |
| 3,394,582 | 7/1968 | Munro | 73/23.1 |
| 3,405,551 | 10/1968 | Halasz | 73/23.1 |
| 3,422,664 | 1/1969 | Ayers | 73/23.1 |

Primary Examiner—Richard C. Queisser
Assistant Examiner—Stephen A. Kreitman

[57] ABSTRACT

A gas chromatographic apparatus especially useful in analyzing low boiling materials is provided with means for flowing a pressurized liquid sample through the sampling valve, during the sampling period, in order to reduce the possibility of trapping bubbles of vaporized sample in the sampling valve.

5 Claims, 1 Drawing Figure

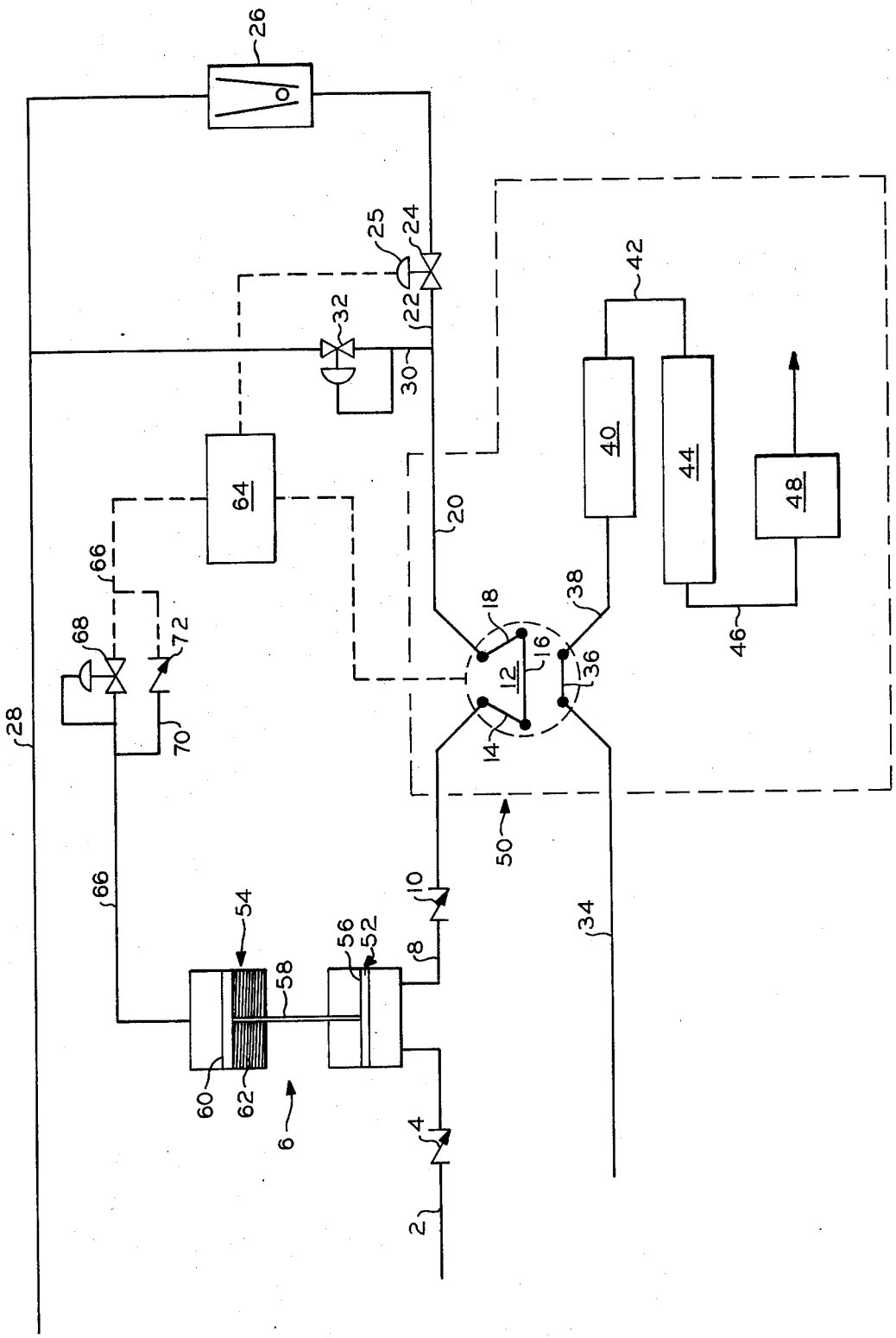

CHROMATOGRAPHIC APPARATUS

This invention relates to the gas chromatographic analysis of fluids. In one aspect, it relates to an improved apparatus for analyzing low boiling materials. In another aspect it relates to an improved method for analyzing low boiling materials by gas chromatography.

Gas chromatography is a known method for analyzing fluid samples by preferential sorption and desorption. The desirability of using chromatography for such specific uses as fractionation control has been recognized for some time. Certain features of process gas chromatography, such as specific measurements, high sensitivity and simplicity of operation make this type of analyzer very attractive for use in automatic process control. There are, however, some inherent features of chromatography which have presented obstacles in adapting gas chromatography to widespread use in process control of all types of process streams.

Conventionally, in the operation of a gas chromatographic analyzer, the sample fluid mixture is introduced into a chromatographic column as a vapor representative of the fluid mixture. To insure reproduceability the aliquot portion of the sample mixture is taken as a liquid.

It is known to introduce a liquid sample onto a chromatographic column by trapping a sample of known volume in a sampling chamber, applying pressure to the trapped sample and injecting same onto the column. In process control gas chromatographic the sampling chamber may be located within the instrument's heated enclosure. When sampling a low boiling fluid using the above sampling system it is possible that the low boiling fluid will commence boiling during sampling, at least partially filling the sampling chamber with bubbles of vaporized sample, thus altering the actual volume of sample delivered to the chromatographic column.

It is therefore an object of this invention to provide a gas chromatographic apparatus having an improved sampling system for analyzing low boiling materials.

Other objects, aspects and advantages of the present invention will be apparent to those skilled in the art from a reading of the following description, the appended claims and the attached drawing.

In accordance with the present invention there is provided a gas chromatographic apparatus for analyzing low boiling materials which comprises, in operable communication, a chromatographic column, means for detecting a property of the effluent from such column, a sampling valve means having a sample chamber of known volume, means for passing a fluid sample stream at a first pressure $P_1$ to the sampling valve means and through the sample chamber, means for increasing the pressure on the fluid sample stream from $P_1$ to a higher pressure $P_2$, valve means downstream of the sample chamber for terminating the flow of sample stream therethrough, means to allow the sample stream to flow through the sample chamber at the pressure $P_2$, and means for introducing a portion of the sample stream at the prssure $P_2$ into the column.

The invention will be better understood by reference to the single drawing which is a schematic representation of the apparatus of this invention.

Referring now to the drawing, a fluid sample stream is introduced via conduit means 2 through check valve means 4 to pressure increasing means 6. The sample passes out of the pressure increasing 6 via conduit means 8 through check valve means 10 to a multi-port sample valve means 12 having an actuating means, not shown. A suitable multi-port sample valve means is described in U.S. Pat. No. 3,111,849. The fluid sample stream is passed through valve means 12 via conduit means 14 to a sample chamber 16 positioned within valve means 12.

The fluid sample stream is passed from sample valve means 12 via conduit means 18 to a vent conduit means 20. The fluid sample stream is then passed via conduit means 22 through shut-off valve means 24 having valve actuator means 25, and flow meter 26 to conduit means 28, or via conduit means 30 through relief valve means 32 to conduit means 28, as will be hereinafter explained.

A carrier gas, such as helium, is passed continuously via conduit means 34 to sample valve means 12. The carrier gas is passed through valve means 12 via conduit means 36 to conduit means 38, thence via conduit means 38 through vaporizer means 40 to chromatographic column 44, containing a suitable packing material capable of selectively retarding the flow of constituents of the sample fluid directed thereto. Vaporizer means 40 is optional. It is used when it is desired to ensure that the fluid sample is completely vaporized prior to entry of same onto the column 44.

The effluent from the chromatographic column 44 is passed via conduit means 46 to a conventional detector means 48 adapted to measure a property of the fluid mixture directed thereto, which property is representative of the composition of the sample fluid. The output signal from the detector means 48 is passed to a suitable recording instrument, not shown, such as a conventional strip chart recorder.

The sample valve means 12, the vaporizer means 40, if used, chromatographic column 44 and detector means 48 are generally housed within a closed chamber, designated generally as 50, which is maintained at a suitable analysis temperature T.

The pressure increasing means, designated generally as 6, preferably includes a pump chamber 52 and a power chamber 54. The pump chamber 52 has a piston 56 connected to a connecting means 58 which is connected to a piston 60 in the power chamber 54. The power chamber 54 is provided with a spring means 62 to return the piston 60 to the top of the chamber 54.

The sample valve means 12, the shut-off valve means 24 and the power chamber 54 are controlled by sequence controller means 64. In the embodiment shown, pneumatic control is employed, although the system is not limited thereto.

Air is supplied to the power chamber 54 via conduit means 66. Pressure regulating means 68 can be provided in the conduit means 66 to regulate the pressure developed in the power chamber 54. Where such pressure regulating means 68 is employed, a by-pass conduit means 70 provided with a check valve 72 is also employed to provide a return flow line for the air from the power chamber 54.

During the non-sampling, non-analyzing mode described above, the sample valve means 12 is in the position shown, the shut-off valve means 24 is open and the piston 56 of the pump chamber 52 is in its uppermost position. The fluid sample stream flows through the conduit means 2, the check valve 4, the pump chamber 52, conduit means 8, check valve 10, conduit means 14, sample chamber 16, conduit means 18, 20 and 22, through cut-off valve means 24, flow meter 26 to conduit means 28, and is then returned to its source or disposed of in suitable manner.

When it is desired to take a sample, the sequence controller means 64 provides air to the actuator means 25 of shut-off valve means 24, shutting the valve means 24. The sequence controller means 64 then provides air to the power chamber 54 through the pressure regulating means 68 and the conduit means 66. The pressure buildup in the power chamber 54 acts against the spring 62 and forces the piston 60 downward, which in turn forces the piston 56 in the pump chamber 52 downward. The check valve 4 prevents the now pressurized portion of the sample fluid stream from flowing back through conduit means 2. At a predetermined pressure, the relief valve means 32 opens, allowing the sample fluid, under pressure, to flow through the conduit means 8, check valve 10, conduit means 14, sample chamber 16 and out via conduit means 18, 20 and 30.

The sequence controller means 64 then actuates the sample valve means 12, causing the liquid sample in the sample chamber 16 to be passed via conduit means 38 to vaporizor 40. The effluent from the vaporizor 40 is passed via conduit means 42 to the chromatographic column 44 for separation therein, as described previously. The sequence controller means 64 then causes the sample valve means 12, the pump means 6 and the shut-off valve means 24 to return to their respective original positions.

The chromatographic analyzer of this invention can be employed for the analysis of any low-boiling fluid normally capable of being analyzed by gas chromatography. In general, the apparatus of the invention can be used for the analysis of any fluid or fluid mixture wherein the temperature of analysis is lower than the lowest critical temperature of the sample components. The critical pressure is of lesser importance inasmuch as the pressure increasing means 6 is generally capable of applying a pressure to the fluid sample in excess of the critical pressure.

The apparatus of this invention is particularly applicable for use in the analysis and control of a process stream comprising butane.

The pressure increasing means 6 can be constructed of stainless steel with inert seals, such as, for example, polytetrafluoroethylene or the like. The power chamber can be a permanently lubricated, single acting springreturn type cylinder. Typical piston diameters of 0.5-inch for the pump chamber and 1.5-inch for the power chamber give a 10:1 ratio of pumped pressure to applied pressure; piston diameters of 0.5-inch and 2.25-inch, respectively, give a 20:1 ratio.

Reasonable variations and modifications, which will be apparent to those skilled in the art, can be made to this invention without departing from the spirit and scope thereof.

What is claimed is:

1. A chromatographic analyzer comprising:
 a chromatographic column to separate the components of a fluid sample introduced to same;
 detecting means in operable communication with said chromatographic column for detecting a property of a fluid representative of the composition thereof;
 sample valve means in operable communication with said chromatographic column, said sample valve means having a sample chamber calibrated to contain a predetermined volume of sample;
 means for maintaining said chromatographic column, said detecting means and said sample valve means at a temperature T;
 conduit means in operable communication with said sample valve means for passing a fluid sample stream at a first pressure $P_1$ to said sample valve means and through said sample chamber;
 valve means downstream of said sample chamber for terminating the flow of sample stream therethrough;
 means in operable communication with said conduit means for increasing the pressure on the portion of said sample stream in said conduit means and in said sample chamber from said pressure $P_1$ to a higher pressure $P_2$, said pressure $P_2$ being sufficient to maintain said sample in the liquid state at said temperature T;
 relief valve means downstream of said sample chamber for allowing said sample stream to flow through said sample chamber at said pressure $P_2$, said relief valve means being normally closed and preset to open at said pressure $P_2$; and
 means for introducing a portion of said sample stream at said pressure $P_2$ into said chromatographic column.

2. The apparatus of claim 1 wherein said pressure increasing means comprises a closed chamber having an inlet and an outlet, said outlet being in operable communication with said conduit means; a piston in sealing contact and slidably disposed within said chamber; means for moving said piston reciprocally within said chamber; means for applying a closing force on said piston; and biasing means for withdrawing said piston when said closing force is withdrawn.

3. The apparatus of claim 1 wherein said sample valve means is a multiport valve means having six ports, moveable between first and second positions, including a valve actuator means, with port one connected to port two, port three to port four and port five to port six in said first position, and with port one connected to port six, port two to port three and port four to port five in said second position, said conduit means being in communication with said port one, said sample chamber being connected between said port two and said port five, said chromatographic column being in communication with said port four, said terminating valve means being in communication with said port six and a source of carrier gas being in communication with said port three.

4. The apparatus of claim 1 further comprising sequence controlling means for sequentially activating said terminating valve means, said pressure inducing means and said means for introducing said sample at said pressure $P_2$ into said chromatogrphic column.

5. The apparatus of claim 1 further comprising means for vaporizing said sample positioned in operable communication between said sample valve means and said chromatographic column.

* * * * *